(12) United States Patent
Ledent

(10) Patent No.: US 9,416,400 B2
(45) Date of Patent: Aug. 16, 2016

(54) METHOD AND DEVICE FOR PRODUCING AND/OR PURIFYING POLYNUCLEOTIDES AND PRODUCTS OBTAINABLE THEREOF

(71) Applicant: EUROGENTEC S.A., Seraing (BE)

(72) Inventor: Philippe Ledent, Liege (BE)

(73) Assignee: EUROGENTEC S.A., Seraing (BE)

( * ) Notice: Subject to any disclaimer, the term of this patent is extended or adjusted under 35 U.S.C. 154(b) by 35 days.

(21) Appl. No.: 14/451,951

(22) Filed: Aug. 5, 2014

(65) Prior Publication Data

US 2014/0342449 A1 Nov. 20, 2014

Related U.S. Application Data

(62) Division of application No. 13/322,869, filed as application No. PCT/EP2010/057276 on May 26, 2010, now Pat. No. 8,822,672.

(30) Foreign Application Priority Data

May 26, 2009 (EP) ..................................... 09161169

(51) Int. Cl.
| | |
|---|---|
| C12M 1/00 | (2006.01) |
| C12M 3/00 | (2006.01) |
| C12Q 1/68 | (2006.01) |
| C07B 63/00 | (2006.01) |
| C12N 15/10 | (2006.01) |

(52) U.S. Cl.
CPC .............. *C12Q 1/6806* (2013.01); *C07B 63/00* (2013.01); *C12N 15/1003* (2013.01)

(58) Field of Classification Search
None
See application file for complete search history.

(56) References Cited

U.S. PATENT DOCUMENTS

| | | | |
|---|---|---|---|
| 4,210,166 A | 7/1980 | Munie | |
| 4,474,477 A | 10/1984 | Smith et al. | |
| 5,316,383 A | 5/1994 | Begemann et al. | |
| 5,743,637 A | 4/1998 | Ogier | |
| 6,410,274 B1 | 6/2002 | Bhikhabhai | |
| 6,664,049 B1 | 12/2003 | Chenvalier | |
| 2002/0127704 A1 | 9/2002 | Arakaki et al. | |
| 2005/0026177 A1 | 2/2005 | Urthaler et al. | |
| 2005/0244947 A1 | 11/2005 | Voss et al. | |

FOREIGN PATENT DOCUMENTS

| | | |
|---|---|---|
| EP | 0 880 536 | 12/1998 |
| EP | 1 462 519 A1 | 9/2004 |
| EP | 2 088 196 A1 | 8/2009 |
| WO | WO 97/23601 | 7/1997 |
| WO | WO 97/29113 | 8/1997 |
| WO | WO 00/09680 | 2/2000 |

OTHER PUBLICATIONS

Birnboim et al., "A rapid alkaline extraction procedure for screening recombinant plasmid DNA," *Nucleic Acids Research* (1979) 7 (6): 1513-1523.

Ferreira et al., "Downstream processing of plasmid DNA for gene therapy and DNA vaccine applications," *Tibtech* (2000) 18: 380-388. XP004214265.

Levy et al., "Biochemical engineering approaches to the challenges of producing pure plasmid DNA," *Tibtech* (2000) 18: 296-305. XP004908535.

Urthaler et al., "Automated alkaline lysis for industrial scale cGMP production of pharmaceutical grade plasmid-DNA," *Journal of Biotechnology* (2007) 128: 132-149. XP002485653.

Urthaler et al., "Improved downstream process for the prodcution of plasmid DNA for gene therapy," *Acta Biochimica Polonica* (2005) 52: 703-711. XP002485654.

*Primary Examiner* — Patrick Lewis

(74) *Attorney, Agent, or Firm* — Merchant & Gould P.C.

(57) ABSTRACT

An apparatus and a method for obtaining a (poly)nucleotide sequence of interest include steps of cultivating hosts cells to produce a nucleotide sequence of interest and harvesting these cells, introducing these cells in a passageway and disintegrating them in a continuous process. In the continuous process, performing in the passageway a precipitation of contaminants by a mixing of the disintegrated cells with a solution containing one or more salt(s) and obtaining a mixture and allowing a precipitate to separate from the solution of this mixture, preferably to float and/or to sediment from the solution of this mixture for 1-48 hours and pumping out a soluble material from this solution, while excluding recovering the precipitate.

23 Claims, 1 Drawing Sheet

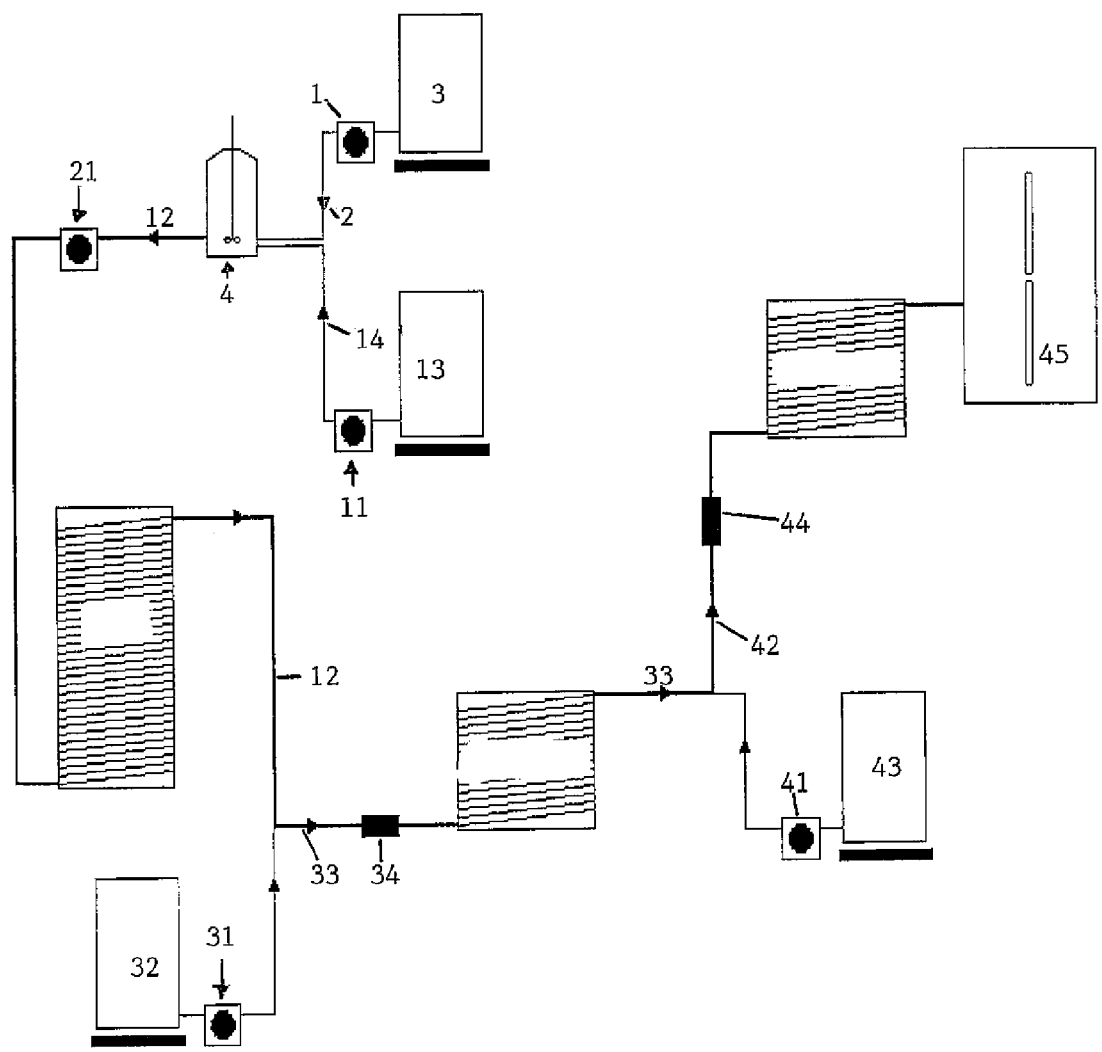

US 9,416,400 B2

METHOD AND DEVICE FOR PRODUCING AND/OR PURIFYING POLYNUCLEOTIDES AND PRODUCTS OBTAINABLE THEREOF

This application is a Divisional application of U.S. Ser. No. 13/322,869 filed 7 Feb. 2012 and issued as U.S. Pat. No. 8,822,672, which is a National Stage Application of PCT/EP2010/057276, filed 26 May 2010, which claims benefit of Serial No. 09161169.9, filed 26 May 2009 in the EPO and which applications are incorporated herein by reference. To the extent appropriate, a claim of priority is made to each of the above disclosed applications.

FIELD OF THE INVENTION

The present invention concerns a method and a device for obtaining (producing and/or purifying) polynucleotide sequences, like a (pharmaceutical grade) plasmid DNA.

STATE OF THE ART

The purification of polynucleotides is generally obtained from host cells able to produce large quantities of these polynucleotides, possibly after genetic engineering.

Birnboim et al., (Nucleic acids research, 1979, 7, 1513-1523) describe the addition of an alkaline solution onto cell culture to disintegrate these cells and probably to denaturate genomic DNA but not plasmid DNA. This alkaline lysis is coupled with neutralization by the use of a sufficient amount of acetate/acetic acid, with one or more filtration step(s) and with a retention step upon a chromatographic column.

It is known that a biomass of gram-negative bacteria, such as *Escherichia coli* can be lysed and its nucleotides sequences of interest separated from the bulk of nucleic acids and proteins by successive steps including a sedimentation, a filtration, a selective precipitation and a specific retention on columns.

Depending on the protocol followed, these nucleotide sequences of interest are combined with contaminants (or impurities), such as endotoxins, phenols, caesium chlorides, ethidium bromides, Triton®, bound proteins or other nucleic acids.

As highly-purified nucleotides sequences are required for specific uses in laboratories or for clinical purposes, several attempts to reduce the amount of contaminants were proposed.

EP 0 880 536 B1 describes a method to obtain endotoxin-pure DNA plasmids based on a separation using a hydroxyapatite chromatography.

U.S. Pat. No. 6,410,274 B1 (WO9916869A1) describes a batch wise method for a plasmid DNA purification via 0.1-0.4 M $CaCl_2$ addition to precipitate contaminants such as genomic DNA and RNA molecules.

The nucleotide sequence (preferably Plasmid DNA) integrity must be guaranteed by the process. Major hurdles prevent easy recoveries of these nucleotide sequences.

For instance, the use of alkaline solution or heating step and/or long procedure degrade these nucleotide sequences. In addition, DNA molecules, including plasmids are sensitive to mechanical stress. Furthermore, highly viscous solution may cause either local heterogeneities or require extensive stirring, both having the potential to degrade these nucleotide sequences. This is especially the case when concentrated chloride of divalent metal (such as $CaCl_2$) solutions are used. To avoid degradation, some processes of the state of the art require handling of a solution at 4° C., which results into higher operational constraints and costs.

It is also known that batch wise methods further present a risk of contamination.

US patent application 2005/0026177 describes a device and a continuous method for obtaining pharmaceutical grade plasmid DNA, including an alkaline lysis, a neutralization and a sedimentation of the precipitate in a retention layer above an outlet, where the cleared lysate leaves the retention reactor.

AIMS OF THE INVENTION

The present invention is related to a method and an apparatus which do not present the drawbacks of the methods and apparatus of the state of the art, especially a cheap and simplified method and apparatus that do not require a chromatographic step or a chromatographic device and that can be preferably performed or used at room-temperature for an efficient and rapid production and/or purification of one or more (poly)nucleotide sequence(s) of interest, such as a viral sequence or a (possibly pharmaceutical (clinical) grade) DNA plasmid of interest.

SUMMARY OF THE INVENTION

The present method for obtaining (by a production and/or purification) a (poly)nucleotide sequence of interest, comprises (or consists of) the steps of:

a) possibly cultivating (preferably recombinant) hosts cells producing (involved in the synthesis of) this (poly)nucleotide sequence, especially this DNA plasmid of interest and harvesting these cells containing this (poly)nucleotide sequence, preferably this plasmid;

b) introducing these cells (producing this (poly)nucleotide sequence, preferably this DNA plasmid of interest) in a passageway and disintegrating these cells (through this passageway) in a continuous process (i.e. continuously in a continuous flow device);

c) in this continuous process (i.e. continuously in this continuous flow device), performing in this passageway a (continuous) precipitation of contaminants (or impurities) of this (poly)nucleotide sequence, especially this DNA plasmid, by mixing these (disintegrated) cells with one or more (hydrated) salt(s) of a divalent ion, preferably a salt selected from the group consisting of (hydrated) $CaCl_2$, (hydrated) $MgCl_2$, (hydrated) $ZnCl_2$, (hydrated) $SrCl_2$ and (hydrated) $BaCl_2$, or (less preferably) other (hydrated) salt(s), such as LiCl, ammonium acetate, amonium sulfate, sodium sulfate or magnesium sulphate (preferred salts being (hydrated) $CaCl_2$ and (hydrated) $MgCl_2$);

d) recovering the obtained mixture (in one vial) and allowing a precipitate to separate (from the solution of the mixture), preferably to float and/or to sediment for a period comprised between about 1 hour and about 48 hours;

e) recovering, preferably by a pumping out, a soluble material comprising this polynucleotide sequence, especially this DNA plasmid from this solution while excluding recovering the precipitate;

f) preferably performing one or more filtration step(s) of this soluble material upon one or more filter(s) having a pore size comprised between about 0.22 μm and about 1.5 μm, preferably followed by an ultra-filtration step upon an about 50 kDa membrane to about 500 kDa membrane (preferably between about 50 and about 250 kDa, more preferably between about 70 and about 100 kDa) to keep a first membrane retentate and recovering the nucleotide sequence of interest to be purified, preferably the DNA plasmid of interest from this first retentate.

More precisely, the present invention is related to a method for obtaining (by a production and/or a purification) a DNA plasmid of interest having a size lower than about 3000 bases (base pairs) and comprising (consisting of) the steps of:
  a) possibly cultivating (preferably recombinant) hosts cells comprising this DNA plasmid of interest and harvesting these cells containing this plasmid;
  b) introducing these cells (comprising the DNA plasmid of interest) in a passageway, performing a treatment with sufficient amount of RNase and disintegrating these cells in continuous process (continuously in a continuous flow device)
  c) in this continuous process (continuously in a continuous flow device), performing in this passageway a (continuous) precipitation of contaminants (or impurities) of this plasmid by a mixing of these (disintegrated) cells with one or more (hydrated) salt(s) of a divalent ion, preferably a salt selected from the group consisting of (hydrated) $CaCl_2$, (hydrated) $MgCl_2$, (hydrated) $ZnCl_2$, (hydrated) $SrCl_2$ and (hydrated) $BaCl_2$, or (less preferably) other (hydrated) salt(s) such as LiCl, ammonium acetate, amonium sulfate, sodium sulfate or magnesium sulphate (preferred salts being (hydrated) $CaCl_2$ and (hydrated) $MgCl_2$);
  d) recovering the obtained mixture (in one vial) and allowing a precipitate to separate (from the solution of the mixture), preferably to float and/or to sediment for a period comprised between about 1 hour and about 48 hours;
  e) recovering, preferably by a pumping out, a soluble material comprising the plasmid from this solution, while excluding recovering the precipitate (and of the sediment and floating elements);
  f) preferably performing one or more filtration step(s) of this soluble material upon one or more filter(s) having a pore size comprised between about 0.22 μm and about 1.5 μm, preferably followed by an ultra-filtration (step) upon an about 50 kDa membrane to about 500 kDa membrane (preferably about 50 to about 250 kDa, more preferably about 70 to about 100 kDa membrane) to keep a first membrane retentate and recovering the plasmid of interest from this first retentate.

The host cell used in the method according to the invention is either a prokaryote cell, such as bacteria or a eukaryote cell, preferably selected from the group consisting of yeast, plants, fungi, insect or mammalian cells (including human cells with the proviso that these mammal cells are non human embryonic cells).

The preferred eukaryote cells of the invention are yeasts, such as *Saccharomyces cerevisiae* cells or *Pichia pastoris* cells and/or animal cells, such as *Drosophilla* S2 cells or Chinese Hamster Ovary (CHO) cells.

Preferably, the host cell is a prokaryote cell, like gram positive or gram negative bacteria, such as *Escherichia coli* or *Bacillus Subtilis* cells.

By the terms "(poly)nucleotide sequence", it is meant any nucleotide sequence of more than 50 base, preferably of more than 50 base pairs. More preferably, this (poly)nucleotide sequence is a DNA molecule.

Preferably, the (poly)nucleotide sequence of the invention is in the form of a (DNA) plasmid, possibly a (DNA) plasmid of a size smaller than 3000 base pairs.

Advantageously, in the method of the invention, the cells (suspension) are disintegrated by an addition of a lysis solution Advantageously, the (lysis) solution to disintegrate cells (suspension) is an alkaline solution, preferably present at a pH comprised between about 11 and about 12.5, preferably at a pH comprised between about 12 and about 12.5.

A preferred method to disintegrate these cells includes the step of mixing (continuous addition) of the cells (suspension) with an alkaline (lysis) solution into the passageway and thereafter obtaining (continuously) in this passageway a neutralization by an addition to the lysed cells of a neutralization solution composed of a sufficient amount of an acetic acid/acetate composition (solution), preferably at a pH comprised between about 5.0 and about 6.0 to form a first mixture.

Advantageously, the pH of this alkaline disintegration (lysis) composition (solution) is comprised between about 12 and about 12.5 and this solution is supplemented with a sufficient amount of one or more detergent(s).

Preferably, this alkaline lysis solution consists of a sufficient amount of NaOH, of $Na_2CO_3$ or of a mixture thereof, and is preferably a sufficient amount of NaOH.

The lysis solution to disintegrate cells may further comprise between about 0.01 and about 5%, preferably between about 0.1 and about 2%, more preferably between about 0.5 and about 1% (w:v) of one or more detergent(s), preferably a detergent selected from the group consisting of Sodium Dodecyl Sulfate (SDS), Sodium Deoxycholate, Triton® X-100, Triton® X-114, Nonidet® P-40, Octyl-glucoside, Brij® 35, Brij® 56 Tween® 20 and CHAPS (3-[(3-Cholamidopropyl)dimethylammonio]-1-propanesulfonate), or a mixture thereof.

Advantageously, the optimal contact time between the cells (suspension) comprising the biological molecule(s) of interest and the (lysis) solution used to disintegrate (continuously) these cells is comprised between about 15 seconds and about 15 minutes, preferably between about 3 minutes and about 10 minutes, more preferably of about 5 minutes.

Alternatively, the optimal contact time between the cells (suspension) comprising the biological molecule(s) of interest and the (lysis) solution used to disintegrate (continuously) these cells is preferably comprised between about 2 minutes and about 3 minutes.

Preferably, the acetic acid/acetate composition has a pH comprised between about 5.0 and about 6.0, preferably of about 5.5.

Preferably, the acetic acid/acetate composition has a concentration of 3 M (mol/l) of acetate and 15% (v:v) of acetic acid.

Preferably, the acetic acid/acetate composition is chilled at about 4° C.

Advantageously, the optimal contact time of these lysed cells comprising the biological molecule(s) of interest and the neutralization solution is comprised between about 15 seconds and about 5 minutes, preferably is between about 30 seconds and about 2 minutes, more preferably of about 1 minute.

Advantageously, the optimal contact time of these lysed cells and this precipitation solution is comprised between about 15 seconds and about 5 minutes, preferably is between about 30 seconds and about 2 minutes, more preferably of about 1 minute.

Advantageously, the optimal time of step d) related to the decantation, the sedimentation and/or the floatation is comprised between about 5 hours and about 24 hours, preferably between about 8 hours and about 24 hours, more preferably between about 20 hours and about 24 hours.

By about, it is preferably meant a value plus or minus 20 or 10% (e.g. about 5 minutes means every values from 4 minutes and 30 seconds to 5 minutes and 30 seconds).

The method of the invention may optionally comprise a preliminary step consisting of the addition of a sufficient amount of RNase to the (whole) cells (suspension) comprising the plasmid of interest and that may diffuse through the cell membrane. This RNase treatment is especially useful for a purification of plasmid DNA having a size inferior to 3000 bases (base pairs).

Preferably, the (hydrated) salt is selected from the group consisting of (hydrated) $CaCl_2$, (hydrated) $MgCl_2$, (hydrated) $ZnCl_2$, (hydrated) $SrCl_2$ and (hydrated) $BaCl_2$, or (less preferably) other (hydrated) salt(s) such as LiCl, ammonium acetate, ammonium sulfate, sodium sulfate or magnesium sulphate (preferred salts being (hydrated) $CaCl_2$ and (hydrated) $MgCl_2$)

and is(are) added (in continuously) to these (disintegrated) cells in a solution at a concentration comprised between about 2M and about 6 M.

The preferred hydrated salt is $CaCl_2.2H_2O$ and that is added at a concentration comprised between about 2 M and about 6 M, preferably at about 5 M.

Advantageously, the optimal contact time between these (disintegrated) cells and the added salt(s) is comprised between about 15 seconds and about 5 minutes, preferably between about 30 seconds and about 2 minutes, more preferably is of about 1 minute, this period being suitable for obtaining the required precipitation without inducing shearing forces that may destroy the biological molecule(s) of interest to purify.

Advantageously, the continuous process of the invention is performed without contact of the solution containing the (poly)nucleotide sequence (preferably the plasmid) of the invention and non-disposable material (such as pumps and means to control the pump output).

In the method of the invention, the continuous process (or the continuous addition steps) is performed via an opening of inlets/outlets, pumps or valves and these pump outputs are advantageously controlled by weighing the vials or recipients of the feeding solutions of the invention.

Preferably, the pumps used in the continuous process and in the device of the invention are peristaltic pumps.

In a less preferred embodiment, this continuous process is performed via an opening of inlets outlets, pumps or valves and these pump outputs are controlled by a measure of the pump outputs into the different tubing elements.

In the method of the invention, the filtration step is done on depth-filters.

Alternatively, in the method of the invention, the filtration step is done on surface filters.

The method of the invention may preferably further comprise a step g) of performing an (polishing step) anion-exchange chromatography, with a washing substep, preferably exactly one (polishing) step upon (anion-exchange) chromatography is performed.

The anion exchange chromatography (step g) comprises (or consist of) classical purification steps well known by the person skilled in the art and comprising the substeps of:
  binding the (poly)nucleotide sequence present in the first retentate
  washing
  eluting the (poly)nucleotide sequence of interest.

The washing substep is preferably performed by using a solution buffered at pH of about 6 to about 10, preferably comprising about 50 mM Tris (HCl) and from about 0.4 to about 0.6 M NaCl.

Optionally, after this washing substep (and before the eluting substep), another washing substep is performed with the same solution supplemented with one or more neutral detergent(s), preferably detergent(s) selected from the group consisting of Triton® X-100, Triton® X-114, Tween® 20, Nonidet® P-40, octylglucoside, Brij® 35, Brij® 56, or a mixture thereof, preferably present in the solution at about 0.1% to about 1%, and is followed by a third washing substep without neutral detergent(s).

The elution step of the first retentate fraction (to collect the first retentate and recover the (poly)nucleotide sequence of interest) is performed by using a salt gradient, preferably by an addition of a buffered solution at pH of about 6 to about 10 and having a salt concentration increasing from about 0.4 M to about 2 M of NaCl, preferably from about 0.5 to about 1 M of NaCl.

Advantageously, these washing and eluting (sub)steps of the anion chromatography according to the method of the invention are performed by adding at least three-time the volume of the column for each solution, preferably by adding (at least) five-time the volume of the column for each solution.

The method of the invention preferably further comprises a step h) of performing an ultrafiltration of the first retentate upon an about 30 kDa membrane and collecting a (newly) obtained (about 30 kDa) membrane second retentate and possibly performing a (final) filtration of this (newly) obtained (about 30 kDa) second retentate upon an about 0.22 µm membrane to recover in the permeate, the purified (from these contaminants or impurities) (poly)nucleotide sequence, preferably the plasmid of the invention.

Advantageously, the method of the invention allows a simplification and a cost reduction of the methods of the state of the art, because it is advantageously performed at room temperature: a temperature comprised between about 15° C. and about 35° C., preferably at a temperature between about 20 and about 25° C.

Alternatively, the whole method of the invention is done at room temperature (a temperature comprised between about 15° C. to about 35° C.), except the step d) done at a temperature of about 4° C. with suitable media that may be used to obtain a cooling of the solution comprising the (poly)nucleotide sequence of interest that improve the mixing and avoid nucleic acids damage.

The invention also relates to an apparatus (device, plant or kit of parts) for carrying the method, preferably the steps b) to c) or all the steps of this method.

Advantageously, this apparatus of the present invention comprises (or consists of) means for obtaining a continuous flow and made of disposable (single use) tubing element (possibly present in a kit of parts), formed with circular tubes, possibly connected to suitable cell reservoir(s) or recipient(s) and having inlet means for the introduction of media and cells (or cells fractions) and outlet means for the collection of contaminants and media separated from collected (poly) nucleotide sequence(s) of interest to be obtained from these cells and purified from these contaminants.

Advantageously, the tubing elements of the invention are in accordance to the requirements for use in human medicine (Pharma quality).

Advantageously, the tubing elements of the invention are non leachable.

The apparatus of the present invention comprises (or consists of) a (first) pump 1 with a pump output of about 0.1 L/min to about 1 L/min, preferably of about 0.30 L/min and linked to a tubing element 2.

In the apparatus of the present invention, this (first) pump 1 is connected to a vial 3 (or a similar recipient comprising or presenting a volume) able to comprise a mixture of cells resuspended, preferably in a 10% (v:v) isotonic aqueous solution buffered at pH about 5 to about 8.

The apparatus of the present invention further comprises a mixing room 4 (a recipient or a bag having a volume suitable) to be placed at the end of the tubing element 2.

Preferably, this tubing element 2 has a total length of 0.5 m to about 5 m, preferably of about 1.5 m.

This tubing element 2 has a preferred internal diameter of about 5 mm to about 25 mm, preferably of about 7 mm to about 15 mm, more preferably of about 9 mm to about 11 mm.

The apparatus of the present invention may further comprise a (second) pump 11 linked by a tubing element 14 to a reservoir 13 or recipient containing a lysis solution, with a pump output of about 0.1 L/min to about 1 L/min, preferably of about 0.30 L/min, and linked to the (tubing) elements of the device through this mixing room 4 or equivalent recipient.

Advantageously, the mixing room 4 is equipped with a disposable orbital homogenizer.

Preferably, the mixing room 4 is a disposable conical vial of about 1 l to about 3 l.

Advantageously, the pump output of the (second) pump 11 is equal to the pump output of the first pump 1.

The apparatus of the present invention may further comprise tubing elements 12 starting from this mixing room 4 or equivalent recipient, these tubing elements 12 having an internal diameter of about 0.5 cm to about 5 cm, preferably of about 1 cm to about 2 cm, more preferably of about 1.27 cm.

The tubing elements 12 have advantageously a total length of about 5 m to about 60 m, preferably of about 10 m to about 30 m, more preferably of about 20 m to about 25 m.

Preferably, at the beginning of the tubing elements 12, the apparatus of the present invention further comprises a (third) pump 21 having a pump output of about 0.2 to about 3 L/min, preferably of about 0.4 to about 1 L/min, more preferably of about 0.6 L/min.

The flow in the tubing element 12 is of about 0.2 to about 3 L/min, preferably of about 0.4 to about 1 L/min, more preferably of about 0.6 L/min.

Preferably, the pump output of the (third) pump 21 is equal to the pump output in the tubing element 12.

Optionally, a (fourth) pump 31, is connected at the end of the tubing elements 12.

This (fourth) pump 31 has a pump output of about 0.2 to about 3 L/min, preferably of about 0.4 to about 1 L/min, more preferably of about 0.6 L/min.

Preferably, the pump output of the (fourth) pump 31 is equal to the pump output in the tubing element 12.

The (fourth) pump 31 is connected (at the end of the tubing element 12 with a reservoir 32 (a bag or an equivalent recipient having an adequate volume) possibly containing the neutralization solution, and linked through a Y-type (or T-type) connection to form a tubing element 33.

Preferably, these tubing elements 33 present means 34 to induce (provoke) an efficient Venturi (mixing) effect in the tubing element 33.

Preferably, the internal diameter of the tubing element 33 is comprised between about 0.5 to about 5 cm, preferably of about 1 cm to about 2 cm, more preferably of about 1.27 cm, excluding means 34 (modified diameter of these tubing elements) used to induce (provoke) the above mentioned Venturi (mixing) effect.

The length of this tubing element 33 is of about 1 m to about 20 m, preferably about 5 m to about 15 m, more preferably about 8 m to about 12 m.

Advantageously, this Venturi (mixing) effect is induced (obtained or provoked) by a reduction in the internal diameter of about 40% (about 50% to about 80% of the initial internal diameter) of the tubing element 33.

The position of the pumps as represented in the enclosed FIG. 1, improves also the efficiency of treatment, because of their respective position as represented, these pumps can advantageously push (the flow of) the fluids in the tubing elements instead of pulling the fluids present in these tubing elements, such pulling movement may induce a collapsing effect of the tubing element(s) that will modify the quality of the product to be recovered.

The apparatus of the present invention further comprises a (fifth) pump 41 connected at the end of the tubing elements 12 or 33, and presenting a pump output of about 0.1 L/min to about 1 L/min, preferably of about 0.3 L/min (linked through a Y-type (or T-type) connection to a tubing element 42.

The (fifth) pump 41 is connected with a reservoir 43 (a bag or a recipient of suitable volume for) containing the precipitation solution and is linked through a Y-type (or T-type) connection at the beginning of the tubing elements 42.

Advantageously, the pumps of the apparatus of the invention are peristaltic pumps.

These tubing elements 42 may also comprise means 44 to induce (provoke) Venturi (mixing) effect.

Advantageously, this Venturi (mixing) effect (in the tubing elements 42 is caused (obtained or provoked) by a reduction in their internal diameter of about 40% (about 50% to about 80% of the initial internal diameter).

By Venturi (mixing) effect, it is meant a turbulence obtained from (induced by) a system, wherein a fluid in laminar flow is forced to pass into reduced tubing in such an extent that the fluid has an increased speed and that a depression is caused just after the reduced diameter.

Preferably, the means to cause Venturi (mixing) effect is placed after about 1 to about 100 cm, preferably after 5 to about 20 cm, more preferably after 9 to about 30 cm of the beginning of tubing elements 33 and/or 42, preferably after the flow in the tubing elements 33 and/or 42 is laminar.

Advantageously, the Venturi (mixing) effect(s) according to the invention allows a mixing of viscous (non-newtonian) fluids that may result into adequate homogenous liquid.

The tubing elements 42 have a total length of about 1 m to about 45 m, preferably of about 5 m to about 15 m, more preferably of about 10 m to about 14 m The tubing elements 42 have an internal tubing diameter of about 0.5 cm to about 5 cm, preferably of about 1 cm to about 2 cm, more preferably of about 1.27 cm, excluding the means to produce this Venturi (mixing) effect.

The apparatus further comprises a filtration device 45 comprising one or more filters.

Preferably, the apparatus of the invention further comprises means to weight the (different) feeding solutions present in the different reservoirs (bags or recipients).

The present invention is also related to a new isolated and purified (from its contaminants) composition comprising this biological molecule of interest obtainable, preferably obtained, by the method here above described.

More particularly, this purified and isolated biological molecule obtained is a DNA plasmid, including DNA plasmid having a size lower than 3000 bases (base pairs).

Preferably, this purified and isolated plasmid DNA composition of the invention is at least contaminants-free: genomic-DNA free, RNA-free and comprises between about 40 and about 100 endotoxin unit/mg DNA (more preferably the plasmid DNA composition comprises about 55 endotoxin unit/mg DNA). This composition that is also advantageously free of chemicals (including RNase) possibly added to the media used in the different method steps of the invention, may also correspond to a pharmaceutical composition comprising an adequate pharmaceutical carrier (or diluent) and a sufficient amount of this biological molecule of interest as above described (purified from its contaminants).

Advantageously, this purified and isolated plasmid DNA composition of the invention is at least contaminants-free: genomic-DNA free, RNA-free and comprises between about 0.2 and about 100 (preferably between about 2 and about 10) endotoxin unit/mg DNA. This composition that is also advantageously free of chemicals (including RNase) possibly added to the media used in the different method steps of the invention, may also correspond to a pharmaceutical composition comprising an adequate pharmaceutical carrier (or diluent) and a sufficient amount of this biological molecule of interest as above described (purified from its contaminants).

Alternatively, the endotoxin content of the plasmide DNA composition is of about 55.

Possibly, the endotoxin content of the plasmide DNA composition is comprised between about 0.2 and about 2 endotoxin unit/mg DNA.

By the term "free", it is meant that the residual content of the contaminant in the composition is less than 2% (w:w), preferably less than 1% (w:w), or less than 0.5% or 0.1% (w:w).

The present invention is described in reference to the enclosed figures in the following preferred examples presented as non-limiting embodiments of the present invention.

DETAILED DESCRIPTION OF THE INVENTION

FIG. 1 illustrates the apparatus or device according to the invention and allowing to carry-out steps a to c of the method of the present invention and being a disposable pipe of about 45.6 meters long, formed with circular tubes (tubing elements).

This apparatus or device is fed in a tubing element 2 comprising the harvested cells at a flow of 0.30 L/min. At about 1.5 m, a pump 11, with a pump output of 0.30 L/min is connected to a reservoir or recipient 13 containing a lysis solution (to disintegrate cells), which is linked to the tubing element 2 through a mixing room 4. The flow is 0.6 L/min.

Optionally, at 21.3 m, another pump 31, with a pump output of 0.6 L/min is connected to a reservoir 32 containing a neutralization solution that is linked through a Y-type (or T-type) connection and where a homogenous non-mechanic mixing is provoked by Venturi effect.

After about 9.5 m, another pump 41, with a pump output of 0.30 L/min and connected with a reservoir 43 containing the precipitation solution that is linked through a Y-type (or T-type) connection and where a homogenous non-mechanic mixing is provoked by another Venturi effect.

After about 11.8 m, means to harvest the mixture are present.

EXAMPLES

Culture

One vial of the GMP master seed is removed from Nitrogen tank (−170° C.) and thawed at room temperature 5 minutes before use, then incubated in adequate medium under shaking at 37° C.

*Escherichia coli* having a plasmid of interest were grown until $OD_{600}$ attained 0.8 units. One culture in the specifications ($OD_{600}$-purity) is selected to inoculate the fermenter.

A sample of the selected culture is taken for Quality Control (QC) tests.

The pH is maintained at 7.0+/−0.2 by periodic addition of NaOH and $HNO_3$. The temperature is maintained to 37+/−0.5° C. and airflow is fixed to 1 vvm (=150 L/min); pressure is regulated to 360 mbars and agitation is fixed to 700 RPM. The fermentation parameters are constant during the fermentation. Small quantities of antifoam are added if needed.

After 15 hours of fermentation, a sample is taken every hour to follow the $OD_{600}$. When the $OD_{600}$ reaches at least 35 units, the culture is cooled below 20° C. During the cooling step, agitation and airflow are reduced to 200 RPM and 40 L/min, respectively.

When the culture temperature is below 20° C., a sample is taken under sterile conditions (for QC tests) and the culture is centrifuged for 20 min at 6700 g in two Beckman Avanti J-20 discontinuous centrifuges equipped with JLA-8.1000 rotor.

The pellets are collected and kept at 4° C. until the end of the fermenter harvest (and centrifugation) step.

The pellets are then resuspended in sterile bags for lysis, or for storage at −20° C.

Lysis and Filtration

The process scale documented hereunder corresponds to 4000 g fresh cell paste equivalent to approximately ⅓ the batch produced in the 100 L fermenter.

The 4000 g of the fresh cell paste are thawed at 2-8° C. during 18+/−3 hours. The thawed suspension is diluted in RM1 buffer to obtain 40 l of suspension (Cell paste 10 fold diluted).

The suspension is then introduced into the passageway at 0.3 L/min; see FIG. 1.

Advantageously, since the passageway is for single use, there is no need of cleaning and/or decontaminating it.

The lysis (cell disintegration) is performed using a continuous system with 2 steps of buffer addition (60L RM2: 200 mM NaOH; 1% w:v SDS and 100 L RM3: 3 M $CH_3COOK$, $CH_3COOH$ 15% v:v)

The first step of lysis (cell disintegration) is performed with the mixing of the cell suspension and of RM2 in a mixing room under orbital stirring (using a single use plastic (polytetrafluoroethylene; PTFE) helix).

The inventors observed that although the lysed solution (disintegrated cells) is viscous, an efficient homogenization was obtained without degrading the plasmid.

The inventors further optimized the tubing lengths and the pump output in order to assess the optimal mean contact time of the cell and the lysis mixture. They found that the system they developed allows short duration such as less than 5 minutes, which advantageously gives a reduced contamination with genomic DNA, and observed an optimum time of 2 or 3 minutes.

The second buffer addition is performed in the tubing system taking advantage of Venturi (mixing) effect in the tubing element 33.

The inventors observed that although the neutralized mixture is very viscous, the use of a Venturi caused an efficient mixing that was obtained without degrading the plasmid (without creating high shearing forces in the liquid).

Given the continuous process, contact time between the cell suspension and RM2 medium is of 5 min, while the contact time between the lysed (disintegrated) cells and RM3 is of one minute.

A solution of 5 M CaCl$_2$.2H$_2$O is then added continuously to the neutralized suspension and the contact time in the passageway is of 1 minute.

Advantageously, no stirring is required to ensure this homogenous mixing since the above-described passageway includes tubular structures with Venturi (mixing) effects and surprisingly allows the formation of a homogenous solution, even after the addition of this very viscous solution. Therefore, no degradation of DNA molecules (that is known to occur under heavy stirring or heavy shearing forces, which is necessary given the high viscosity of a 5 M CaCl$_2$ solution) is observed in the present invention.

The mixture is harvested in a 300 l bag and stored either at 2-8° C. or at room temperature over-night (20+/−4 hours) to allow to settle.

The inventors observed that contaminants both sedimented (a thin layer) and floated at the top of the mixture (in majority). Therefore, the clarified phase is in the middle part of the 300 L bag.

The clarified phase (representing about 80 to 90%) is delicately pumped out of the 300 l bag (with minimising liquid movements in the bag to avoid a re-suspension of the flocs) and harvested in a 200 l Tank liner and further decanted during at least 20 minutes.

The clarified phase is filtered successively on three filters of 1.5 μm, and two of 0.2 μm.

The filtrated phase is harvested and stored.

The ultrafiltration is conducted on 100 kDa PES membranes or alternatively on 70 kDa membranes (for plasmids shorter than 3000 base pairs).

The inventors measured the purity of an aliquot of the retained plasmid and observed a contamination of about 50 to 100 endotoxin unit (EU)/mg DNA, and more generally of about 55 EU/mg DNA. The inventors conclude that this level was remarkable, since no real purification steps were performed yet.

The ultrafiltrated solution is then diafiltered.

The ultrafiltrated solution cleared from contaminants is submitted to anion exchange chromatography. The inventors tested several anion exchange chromatographies. The skilled person may easily find the most suitable one.

Washing steps are performed with a solution of 50 mM Tris (—HCl), 0.54 M NaCl, pH 8.5

Optionally, one washing is done 50 mM Tris (—HCl), 0.54 M NaCl, pH 8.5 supplemented with 0.1 to 1% of Triton X-100, prior to washing steps with 50 mM Tris (—HCl), 0.54 M NaCl, pH 8.5.

The elution is performed by a linear gradient made of mixing of a solution of 50 mM Tris (HCl) pH 8.5 supplemented with 0.54 M NaCl with a solution of 50 mM Tris (HCl) pH 8.5 supplemented with 1 M NaCl.

The eluted material is ultra-filtered on a 30 kDa membrane, then the concentrated retentate is filtered through a 0.22 μm filter, and the filtrate is collected and stored at −20° C.

RNA level is undetectable by HPLC (below the limit of detection). Protein content is below 10 μg/mg of plasmid.

After the chromatographic step, the inventors measured an endotoxin content of about 2 to about 10 units/mg DNA.

Endotoxin is measured by the chromogenic limulus amoebocyte lysate method (KQCL). Endotoxins activate a proenzyme in the KQCL reagent that catalyses the splitting of the chromogenic substrate, which is continuously measured photometrically, at 405 nm, throughout the incubation period. A log/log correlation between the time required for the appearance of color (reaction time) and the endotoxin concentration is linear from 0.005 to 50 EU/ml. The concentration of endotoxin in a sample is calculated from its reaction time by comparison to the reaction time of solutions containing known amounts of endotoxin standard.

When the chromatographic step was performed, the endotoxin content dropped to about 1.42 unit/mg DNA.

Alternatively, when the whole process, including the chromatographic step was optimized, the endotoxin content dropped to about 0.2 unit/mg DNA.

The plasmid recovery is about 30%. However, the inventors found that this ratio may be increased at the expense of purity, and the skilled person may find the best solution depending on the experiment requirements.

The invention claimed is:

1. An apparatus for obtaining a polynucleotide from cells or cell fractions, the apparatus comprising:
a vial for housing the cells or cell fractions, and a first tubing element fluidly connecting and extending from the vial to a mixing chamber, and a first pump connected to the first tubing element;
a first reservoir for housing a first lysing solution, a second tubing element fluidly connecting and extending from the first reservoir to the mixing chamber, and a second pump connected to the second tubing element, said second pump having a pump output between 0.1 L/min and 1 L/min;
a third tubing element extending from said mixing chamber to a tubing connection and having an internal diameter between 0.5 cm and 5 cm and a length between 5 m to 60 m;
a second reservoir for housing a neutralizing solution, a fourth tubing element fluidly connecting and extending from the second reservoir to the tubing connection, and a third pump connected to the fourth tubing element, the third pump having a pump output between 0.2 L/min and 3 L/min;
at least one tubing mixing element constructed to induce Venturi mixing, wherein the tubing connection has an input side and an output side, and wherein the third and fourth tubing elements are connected to the input side and the at least one tubing mixing element constructed to induce Venturi mixing is disposed in a fifth tubing element connected to the output side of the tubing connection, wherein the fifth tubing element has an internal diameter between about 0.5 cm and about 5 cm and a length between about 1 m and about 20 m; and
an outlet for collecting the polynucleotide.

2. The apparatus of claim 1, wherein the first pump has a pump output comprised between 0.1 L/min and 1 L/min.

3. The apparatus of claim 1 comprising a fourth pump linked to a third reservoir connected to the fifth tubing element, said fourth pump having an output of 0.2 L/min to 3 L/min.

4. The apparatus of claim 1, further comprising at the beginning of the third tubing element, a fifth pump having a pump output of 0.2 L/min to 3 L/min.

5. The apparatus of claim 1, wherein the tubing connection comprises a Y-type or T-type connection.

6. The apparatus of claim 3, wherein the fourth pump is connected to the fifth tubing element via a Y-type or T-type connection.

7. The apparatus of claim 1, wherein the first pump, the second pump and the third pump are peristaltic pumps.

8. The apparatus of claim 3, wherein the fourth pump is a peristaltic pump.

9. The apparatus of claim 4, wherein the fifth pump is a peristaltic pump.

10. The apparatus of the claim 1 further comprising weighing means of the first reservoir, of the second reservoir and/or of the vial.

11. The apparatus of claim 3 further comprising weighing means of the third reservoir.

12. The apparatus of claim 1 further comprising a second tubing mixing element constructed to induce Venturi mixing.

13. The apparatus of claim 1, wherein the third reservoir contains a precipitation solution.

14. The apparatus of claim 1, wherein the lysis solution is an alkaline solution at a pH comprised between 11 and 12.5.

15. The apparatus of claim 1, wherein the vial further comprises RNase.

16. The apparatus of claim 13, wherein the precipitation solution comprises salts selected from the group consisting of $CaCl_2$, $MgCl_2$, $ZnCl_2$, $SrCl_2$ and $BaCl_2$, LiCl, ammonium acetate, ammonium sulfate, sodium sulfate and magnesium sulfate and a mixture thereof.

17. The apparatus of claim 16, wherein the salts are present in the precipitation solution at a concentration comprised between 2 M and 6 M.

18. The apparatus of claim 1, wherein the neutralizing solution is an acetic acid solution or an acetate solution at a pH between 5.0 and 6.0.

19. The apparatus of claim 1, wherein the mixing chamber comprises a homogenizer.

20. The apparatus of claim 1, wherein the fifth tubing element connected to a filtration device comprising one or more filters.

21. The apparatus of claim 20, wherein the filters are selected from the group consisting of depth-filters and surface filters.

22. The apparatus of claim 20, wherein the filters have a pore size between 0.22 µm and 1.50 µm.

23. The apparatus of claim 20, wherein the filtration device further comprises an ultra-filtration membrane, from 50 kDa to 500 kDa membrane.

* * * * *